(12) United States Patent
Nguyen et al.

(10) Patent No.: US 9,101,741 B2
(45) Date of Patent: Aug. 11, 2015

(54) TENSIONING PROCESS FOR COATING BALLOON

(75) Inventors: Binh T. Nguyen, Newark, CA (US); Benjamyn Serna, Gilroy, CA (US)

(73) Assignee: ABBOTT LABORATORIES, Santa Clara, CA (US)

( * ) Notice: Subject to any disclaimer, the term of this patent is extended or adjusted under 35 U.S.C. 154(b) by 896 days.

(21) Appl. No.: 13/280,067

(22) Filed: Oct. 24, 2011

(65) Prior Publication Data
US 2012/0128863 A1 May 24, 2012

Related U.S. Application Data

(63) Continuation-in-part of application No. 12/882,953, filed on Sep. 15, 2010, now Pat. No. 8,702,650, and a continuation-in-part of application No. 12/882,990, filed on Sep. 15, 2010, now abandoned.

(60) Provisional application No. 61/345,575, filed on May 17, 2010.

(51) Int. Cl.
| | |
|---|---|
| *A61M 25/10* | (2013.01) |
| *B05C 11/00* | (2006.01) |
| *B05D 7/02* | (2006.01) |
| *A61F 2/958* | (2013.01) |
| *B05D 3/12* | (2006.01) |

(52) U.S. Cl.
CPC ............. *A61M 25/1029* (2013.01); *B05D 7/02* (2013.01); *A61F 2002/9583* (2013.01); *A61F 2250/0067* (2013.01); *A61M 2025/105* (2013.01); *A61M 2025/1031* (2013.01); *B05D 3/12* (2013.01)

(58) Field of Classification Search
CPC .................... A61M 2025/105; A61M 25/1029
See application file for complete search history.

(56) References Cited

U.S. PATENT DOCUMENTS

| | | |
|---|---|---|
| 4,743,465 A | 5/1988 | Saeki et al. |
| 4,748,982 A | 6/1988 | Horzewski et al. |
| 5,300,085 A | 4/1994 | Yock |
| 5,370,614 A | 12/1994 | Amundson et al. |
| 5,464,650 A | 11/1995 | Berg et al. |
| 5,496,346 A | 3/1996 | Horzewski et al. |
| 5,591,227 A | 1/1997 | Dinh et al. |
| 5,626,600 A | 5/1997 | Horzewski et al. |
| 5,649,977 A | 7/1997 | Campbell |
| 5,911,452 A | 6/1999 | Yan |

(Continued)

OTHER PUBLICATIONS

U.S. Appl. No. 13/108,283, filed May 16, 2011, Gong et al.

(Continued)

*Primary Examiner* — Cachet Sellman
(74) *Attorney, Agent, or Firm* — Baker Botts L.L.P.

(57) ABSTRACT

Method of coating an expandable member includes providing an expandable member having a proximal and a distal end with a guidewire lumen extending therebetween, the expandable member having a deflated and fully expanded configurations, and inflating the expandable member to an initial inflation pressure; positioning a mandrel within the guidewire lumen; tensioning the mandrel to straighten the guidewire lumen within the expandable member; and disposing a therapeutic agent on at least a portion of the expandable member. Method further includes partially deflating the expandable member to an intermediate pressure, and drying the therapeutic agent on the expandable member, and, if a folded expandable member is used, at least partially refolding the expandable member.

29 Claims, 13 Drawing Sheets

(56) References Cited

U.S. PATENT DOCUMENTS

| | | | |
|---|---|---|---|
| 5,980,972 | A | 11/1999 | Ding |
| 6,120,847 | A | 9/2000 | Yang et al. |
| 6,141,855 | A * | 11/2000 | Morales .......................... 29/516 |
| 6,406,457 | B1 | 6/2002 | Wang et al. |
| 6,478,807 | B1 | 11/2002 | Foreman et al. |
| 6,494,906 | B1 | 12/2002 | Owens |
| 6,669,980 | B2 | 12/2003 | Hansen |
| 6,676,987 | B2 | 1/2004 | Zhong et al. |
| 6,743,462 | B1 | 6/2004 | Pacetti |
| 7,241,344 | B2 | 7/2007 | Worsham et al. |
| 7,335,227 | B2 | 2/2008 | Jalisi |
| 7,378,105 | B2 | 5/2008 | Burke et al. |
| 7,445,792 | B2 | 11/2008 | Toner et al. |
| 7,455,876 | B2 | 11/2008 | Castro et al. |
| 7,488,337 | B2 * | 2/2009 | Saab et al. .................... 606/192 |
| 7,504,125 | B1 | 3/2009 | Pacetti et al. |
| 7,524,527 | B2 | 4/2009 | Stenzel |
| 2001/0021419 | A1 | 9/2001 | Luthje et al. |
| 2004/0062875 | A1 | 4/2004 | Chappa et al. |
| 2004/0073284 | A1 | 4/2004 | Bates et al. |
| 2004/0122465 | A1 * | 6/2004 | McMurtry et al. ............ 606/194 |
| 2004/0234748 | A1 | 11/2004 | Stenzel |
| 2005/0196518 | A1 | 9/2005 | Stenzel |
| 2005/0233061 | A1 | 10/2005 | Schwarz |
| 2006/0069427 | A1 | 3/2006 | Savage et al. |
| 2007/0031611 | A1 | 2/2007 | Babaev |
| 2007/0088255 | A1 | 4/2007 | Toner et al. |
| 2007/0179591 | A1 | 8/2007 | Baker et al. |
| 2008/0113081 | A1 * | 5/2008 | Hossainy et al. .............. 427/2.1 |
| 2009/0226598 | A1 | 9/2009 | Feng et al. |
| 2010/0023108 | A1 | 1/2010 | Toner et al. |
| 2010/0030183 | A1 | 2/2010 | Toner et al. |
| 2010/0040766 | A1 | 2/2010 | Chappa et al. |
| 2010/0055294 | A1 | 3/2010 | Wang et al. |
| 2010/0310183 | A1 | 12/2010 | Kendall et al. |
| 2011/0151199 | A1 | 6/2011 | Nelson et al. |
| 2011/0281019 | A1 | 11/2011 | Gong et al. |
| 2011/0281020 | A1 | 11/2011 | Gong et al. |
| 2012/0022540 | A1 | 1/2012 | Chasmawala et al. |
| 2012/0064223 | A1 | 3/2012 | Gamez et al. |
| 2012/0065583 | A1 | 3/2012 | Serna et al. |
| 2012/0143054 | A1 | 6/2012 | Eaton et al. |
| 2012/0315374 | A1 | 12/2012 | Nguyen et al. |
| 2012/0315375 | A1 | 12/2012 | Shen et al. |
| 2012/0315376 | A1 | 12/2012 | Nguyen et al. |
| 2014/0072695 | A1 | 3/2014 | Shen et al. |
| 2014/0113059 | A1 | 4/2014 | Shen et al. |
| 2014/0188045 | A1 | 7/2014 | Serna et al. |

OTHER PUBLICATIONS

U.S. Appl. No. 12/882,990, filed Sep. 15, 2010.
U.S. Appl. No. 13/158,057, filed Jun. 10, 2011.
U.S. Appl. No. 13/158,101, filed Jun. 10, 2011.
U.S. Appl. No. 13/158,131, filed Jun. 10, 2011.
U.S. Appl. No. 12/882,953, filed Sep. 15, 2010.
Unverdoben, Martin, "The Paclitaxel-Eluting PTCA-Balloon Catheter in Coronary Artery Disease PEPCAD I-SVD PEPCAD II-ISR",Clinical Research Institute, Center for Cardiovascular Diseases, 2005-2006, Rotenburg/Fulda, Germany.
U.S. Appl. No. 14/078,212, filed Nov. 12, 2013.
U.S. Appl. No. 12/882,953, Dec. 9, 2013 Notice of Allowance.
U.S. Appl. No. 12/882,953, Nov. 15, 2013 Request for Continued Examination (RCE).
U.S. Appl. No. 12/882,953, Oct. 28, 2013 Advisory Action.
U.S. Appl. No. 12/882,953, Oct. 16, 2013 Response to Final Office Action.
U.S. Appl. No. 13/109,156, Oct. 25, 2013 Applicant Initiated Interview Summary.
U.S. Appl. No. 13/158,057, Oct. 24, 2013, Applicant Initiated Interview Summary.
U.S. Appl. No. 12/882,990, Dec. 2, 2013 Amendment and Request for Continued Examination (RCE).
U.S. Appl. No. 12/882,990, Oct. 11, 2013 Advisory Action.
U.S. Appl. No. 12/882,990, Oct. 1, 2013 Response to Final Office Action.
U.S. Appl. No. 13/108,283, Nov. 12, 2013 Issue Fee payment.
U.S. Appl. No. 13/158,101, Oct. 7, 2013 Notice of Allowance.
U.S. Appl. No. 13/108,283, filed May 16, 2011 (Nov. 17, 2011).
U.S. Appl. No. 12/882,953, Jan. 15, 2013 Non-Final Office Action.
U.S. Appl. No. 12/882,990, Dec. 6, 2012 Non-Final Office Action.
U.S. Appl. No. 12/882,953, Mar. 7, 2014 Issue Fee payment.
U.S. Appl. No. 12/882,990, Dec. 19, 2013 Non-Final Office Action.
U.S. Appl. No. 13/158,131, Mar. 13, 2014 Non-Final Office Action.
U.S. Appl. No. 13/109,156, Mar. 20, 2014 Response to Final Office Action.
U.S. Appl. No. 12/882,990, Apr. 8, 2013 Response to Non-Final Office Action.
U.S. Appl. No. 13/108,283, Mar. 28, 2013 Non-Final Office Action.
U.S. Appl. No. 12/882,953, Apr. 12, 2013 Response to Non-Final Office Action.
U.S. Appl. No. 13/158,101, Apr. 26, 2013 Restriction Requirement.
U.S. Appl. No. 13/109,156, Apr. 26, 2013 Restriction Requirement.
U.S. Appl. No. 13/158,057, Apr. 26, 2013 Restriction Requirement.
U.S. Appl. No. 14/078,212, Jun. 6, 2014 Non-Final Office Action.
U.S. Appl. No. 13/109,156, Sep. 10, 2013 Non-Final Office Action.
U.S. Appl. No. 12/882,953, Aug. 16, 2013 Final Office Action.
U.S. Appl. No. 13/158,057, Sep. 12, 2013 Non-Final Office Action.
U.S. Appl. No. 12/882,990, Aug. 1, 2013 Final Office Action.
U.S. Appl. No. 13/108,283, Aug. 12, 2013 Notice of Allowance.
PlumbingSupply.com, "Pipe Hangers and Brackets", (Feb. 2001), www.plumbingsupply.com/pipehangers.htlm.
Vivekanandhan, et al., "Computer-Aided Torch Trajectory Generation for Automated Coating of Parts with Complex Surfaces", *Journal of Thermal Spray Technology*, 3(2):208-215 (1994).
Cornell, Maintaining Distance Using Sonar video, Youtube (2010) http://www.youtube.com/watch?v=Pj6Jxo2Sqgw, [Downloaded on Sep. 16, 2013].
U.S. Appl. No. 13/158,057, Oct. 10, 2014 Notice of Allowance.
U.S. Appl. No. 13/109,156, Oct. 7, 2014 Notice of Allowance.
U.S. Appl. No. 13/158,131, Sep. 29, 2014 Final Office Action.

* cited by examiner

TENSIONING PROCESS FOR COATING BALLOON

REFERENCE TO RELATED APPLICATIONS

This application is a continuation-in-part of U.S. patent application Ser. No. 12/882,953, filed on Sep. 15, 2010, now U.S. Pat. No. 8,702,650, and U.S. patent application Ser. No. 12/882,990, filed on Sep. 15, 2010 now abandoned, and claims the priority to U.S. provisional application Ser. No. 61/345,575, filed on May 17, 2010, the contents of each of which is hereby incorporated by reference in its entirety.

BACKGROUND OF THE DISCLOSED SUBJECT MATTER

1. Field of the Disclosed Subject Matter

The presently disclosed subject matter is related to coating interventional medical devices, and particularly coating of therapeutic agents on an expandable member of a medical device. More particularly, the presently disclosed subject matter relates to a system and method for retaining a therapeutic agent on a balloon during processing and delivery of the medical device.

2. Description of Related Subject Matter

Atherosclerosis is a disease affecting arterial blood vessels. It is a chronic inflammatory response in the walls of arteries, which is in large part due to the accumulation of lipid, macrophages, foam cells and the formation of plaque in the arterial wall. Atherosclerosis is commonly referred to as hardening of the arteries, although the pathophysiology of the disease manifests itself with several different types of lesions ranging from fibrotic to lipid laden to calcific. Angioplasty is a vascular interventional technique involving mechanically widening an obstructed blood vessel, typically caused by atherosclerosis.

During angioplasty, a catheter having a folded balloon is inserted into the vasculature of the patient and is passed to the narrowed location of the blood vessel, at which point the balloon is inflated to a fixed size as a result of fluid pressure inside the balloon. Percutaneous coronary intervention (PCI), commonly known as coronary angioplasty, is a therapeutic procedure to treat the stenotic coronary arteries of the heart, often found in coronary heart disease. In contrast, peripheral angioplasty, commonly known as percutaneous transluminal angioplasty (PTA), generally refers to mechanical widening of blood vessels other than the coronary arteries. PTA is most commonly used to treat narrowing of the leg arteries, especially, the iliac, external iliac, superficial femoral and popliteal arteries. PTA can also treat narrowing of veins, and other blood vessels.

Although the blood vessel is often successfully widened by angioplasty, sometimes the treated wall of the blood vessel undergoes vasospasm, or abrupt closure after balloon inflation or dilatation, causing the blood vessel to collapse after the balloon is deflated or shortly thereafter. One solution to this abrupt closure is stenting the blood vessel to prevent collapse. A stent is a device, typically a metal tube or scaffold, that is inserted into the blood vessel after, or concurrently with angioplasty, to hold the blood vessel open.

While the advent of stents eliminated many of the complications of abrupt vessel closure after angioplasty procedures, within about six months of stenting, a re-narrowing of the blood vessel can form. This is a condition known as restenosis. Restenosis was discovered to be a response to the injury of the angioplasty procedure and is characterized by a growth of smooth muscle cells—analogous to a scar forming over an injury. To address this condition, drug eluting stents were developed to reduce the reoccurrence of the narrowing of blood vessels after stent implantation. A drug eluting stent generally is a metal stent that has been coated with a drug that is known to interfere with the process of re-narrowing of the blood vessel (restenosis). Examples of various known drug eluting stents are disclosed in U.S. Pat. No. 5,649,977 to Campbell; U.S. Pat. No. 5,464,650 to Berg, et al.; U.S. Pat. No. 5,591,227 to Dinh, et al., U.S. Pat. No. 7,378,105 to Burke, et al., U.S. Pat. No. 7,445,792 to Toner, et al., and U.S. Pat. No. 7,335,227 to Jalisi, each of which is hereby incorporated by reference in its entirety. However, a drawback of drug eluting stents is a condition known as late stent thrombosis, which generally is an event wherein blood may clot on the stent.

Drug eluting balloons are believed to be a viable alternative to drug eluting stents in the treatment of atherosclerosis. In a study that evaluated restenosis, and the rate of major adverse cardiac events such as heart attack, bypass, repeat stenosis, or death in patients treated with drug eluting balloons and drug eluting stents, the patients treated with drug eluting balloons experienced only 3.7% restenosis and 4.8% MACE (major adverse cardiac events) as compared to patients treated with drug eluting stents, in which restenosis was 20.8% and 22.0% MACE rate. (See, PEPCAD II study, Rotenburg, Germany).

However, drug eluting balloons present certain unique challenges. For example, the drug carried by the balloon needs to remain on the balloon during delivery to the lesion site, and released from the balloon surface to the blood vessel wall when the balloon is expanded at the lesion site. For coronary procedures, the balloon is typically inflated for less than one minute, typically about thirty seconds. The balloon can be expanded for a longer period of time for peripheral procedures although this time rarely exceeds 5 minutes. Due to the short duration of contact of the drug coated balloon surface with the blood vessel wall, the balloon coating must exhibit efficient therapeutic agent transfer and/or efficient drug release during inflation. Thus, there are challenges specific to drug delivery via a drug coated or drug eluting balloon that are not presented by a drug eluting stent.

Conventional methods of loading interventional devices with therapeutic agents often require coating the entire surface of the balloon with the therapeutic agent. Coating of the entire surface can be performed in the inflated condition. For purpose of storage and shipping, as well as delivery through vasculature, the balloon is folded when deflated. However, once coated with a therapeutic agent, the balloon can become difficult to fold and sheath for assembly of the catheter. Further, conventional equipment and processes used to achieve such folding and assembly can cause damage, loss, or contamination of the therapeutic agent, and/or can result in contamination of the equipment. For example, conventional techniques for coating and folding the balloon require that the balloon be coated and subsequently dried in an expanded condition and thereafter collapsed into the completely folded configuration. This folding operation can cause fragmentation of the dried coating, which can dislodge from the balloon surface, and/or cracking, which effectively increases the surface area of the coating in contact with blood during delivery. Consequently, conventional coating and folding techniques can result in a drug loss of between 10% to 60% of the target dose.

Alternatively, balloons can be coated with a therapeutic agent while in a folded condition, thereby avoiding the drawbacks listed above. However, applying a coating of a solution to a folded balloon results in only a partially coated balloon surface area, which may not be desirable depending upon the needs and application. Furthermore, the entire surface area of a coating applied to the folded balloon is exposed to the blood stream during the tracking and delivery procedure, thus increasing the likelihood of losing a significant amount, if not all, of the drug coating before positioning the balloon and therapeutic agent at the desired location to commence treatment.

Thus, there remains a need for, and an aim of the disclosed subject matter is directed towards, a method with corresponding apparatus for assembly of an expandable member having one or more therapeutic agents coated thereon in such a manner that does not result in unacceptable damage or loss of therapeutic agent, nor significant contamination of the equipment employed, during processing or delivery of the medical device.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims herein, as well as from the appended drawings.

To achieve these and other advantages and in accordance with the purpose of the disclosed subject matter, as embodied and broadly described, the disclosed subject matter includes systems and methods for assembly of an expandable member having one or more therapeutic agents coated thereon. In accordance with an aspect of the disclosed subject matter, a method includes providing an expandable member having a proximal end and a distal end with a guidewire lumen extending therebetween, wherein the expandable member has a deflated configuration and a fully expanded configuration at a nominal pressure. Additionally, a catheter shaft can extend from the proximal end of the expandable member with the guidewire lumen extending through at least a portion of a length of the catheter shaft.

The expandable member is inflated to an initial inflation pressure of from about 10% to about 300% of nominal pressure. The nominal pressure can be from about 6 to about 12 atmospheres, although generally the initial inflation pressure of the expandable member is less than nominal pressure. In one embodiment, the initial inflation pressure is from about 20% to about 100% of nominal pressure, although generally the expandable member is less than the fully expanded configuration. The inflation medium generally is a gas.

A mandrel is positioned within the guidewire lumen of the expandable member, which mandrel has a proximal end portion and a distal end portion. The method includes tensioning the mandrel to straighten the guidewire lumen within the expandable member. The mandrel has a length sufficient to extend at least between the proximal end and the distal end of the expandable member. In another embodiment, the mandrel has a length sufficient to further extend at least the length of the guidewire lumen in the catheter shaft. The mandrel can be made of metal, metal alloy, or polymeric material. In one embodiment, the tensioning can include securing the distal end portion of the mandrel in position, and applying a tension force at a select location of the mandrel. Additionally, or alternatively, the tensioning can include positioning a stopper at the proximal end portion of the mandrel and urging the catheter shaft in the proximal direction against the stopper, such as by applying a tension force to the catheter shaft using a spring or the like.

A therapeutic agent is disposed on at least a portion of the inflated expandable member. Various coating techniques can be employed, including spraying, dipping, syringe coating, electrospinning, electrostatic coating, direct coating, or a combination thereof. In one embodiment, the therapeutic agent is disposed on at least a portion of the expandable member at the initial inflation pressure after tensioning the mandrel to straighten the guidewire lumen. The therapeutic agent can be selected from the group consisting of everolimus, zotarolimus, rapamycin, biolimus, myolimus, novolimus, deforolimus, tacrolimus, temsirolimus, pimecrolimus, paclitaxel, protaxel, taxanes or a combination thereof although other fluids and therapeutic agents are contemplated. In one embodiment the therapeutic agent includes a mixture of at least one excipient and/or at least one solvent.

After disposing the therapeutic agent, the expandable member is partially deflated to an intermediate pressure. The intermediate pressure is generally between about 1% to about 100% of nominal pressure, depending upon the initial pressure used. For example, the intermediate pressure can be from about 10% to about 50% of nominal pressure, or about 10% to about 20% of nominal pressure. As embodied herein, the expandable member is partially deflated to an intermediate pressure after tensioning the mandrel to straighten the guidewire lumen. Deflating the expandable member can include exposing the expandable member to ambient conditions to reach the intermediate pressure, or applying a negative pressure to reach the intermediate pressure.

In accordance with another aspect of the disclosed subject matter, if a folded balloon is used as the expandable member, the expandable member is partially deflated to an intermediate pressure by withdrawing an initial amount of inflation medium from the expandable member, and applying an external force to the expandable member. The initial amount of inflation medium can be withdrawn simultaneously with the application of an external force. After partially deflating the expandable member, a remaining amount of inflation medium can be withdrawn from the expandable member, and/or an external force can be applied to refold the expandable member. For example, withdrawing the remaining amount of inflation medium can occur by drawing a vacuum on the expandable member, for example, by using a vacuum box, indeflator, syringe pump at a rate of approximately 2 ml/min or less. The external force can be applied to the expandable member mechanically, hydraulically or pneumatically, e.g., by a stent crimper. The external force can be applied as a substantially uniform force, applied at select locations of the expandable member, and/or include a torsional component. In one embodiment, the external force is applied to the expandable member by a stent crimper in the range of from about 0.2 to about 0.25 PSI per mm of the expandable member length. At least a portion of the expandable member can be covered with or inserted into a sheath.

The therapeutic agent on the expandable member can be dried throughout or at select stages of the method, e.g., by heating the expandable member, and/or by exposing the expandable member to an air stream of variable temperature or flow rate. In one embodiment, the therapeutic agent is dried after tensioning the mandrel to straighten the guidewire lumen.

Additionally, the disclosed subject matter includes a system for coating an expandable member having a proximal end and a distal end with a guidewire extending therebetween, the system comprising an inflator to inflate an expandable member to an initial inflation pressure, the initial inflation pressure being from about 10% to about 300% of nominal pressure; and a mandrel having a proximal end portion and a distal end portion disposed within the guidewire lumen. The system also includes a tension assembly to tension the mandrel to straighten the guidewire lumen, and a dispenser to dispose a therapeutic agent on at least a portion of an expandable member inflated to the initial inflation pressure. A deflation station is provided to partially deflate an expandable member by reducing the pressure within the expandable member to an intermediate pressure, for example from about 1% to about 100% of nominal pressure. The deflation station can be configured to withdraw an amount of inflation medium from the inflated expandable member and, if a folded balloon is used, to apply an external force to an expandable member. A drying station is also included to dry the therapeutic agent on the expandable member.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

DETAILED DESCRIPTION

Reference will now be made in detail to embodiments of the disclosed subject matter, examples of which are illustrated in the accompanying drawings. The method and corresponding steps of the disclosed subject matter will be described in conjunction with the detailed description of the system.

According to one aspect of the disclosed subject matter, a method of coating an expandable member is provided. The method includes providing an expandable member having a proximal end and a distal end with a guidewire lumen extending therebetween, the expandable member having a deflated configuration and a fully expanded configuration at a nominal pressure. The expandable member is inflated to an initial inflation pressure of from about 10% to about 300% of nominal pressure. A mandrel is positioned within the guidewire lumen, the mandrel having a proximal end portion and a distal end portion. The mandrel is tensioned to straighten the guidewire lumen within the expandable member. A therapeutic agent is disposed on at least a portion of the expandable member at the initial inflation pressure. The expandable member is partially deflated to an intermediate pressure of from about 1% to about 100% of nominal pressure and the therapeutic agent is dried on the expandable member.

According to another aspect of the disclosed subject matter, a system for coating the expandable member is provided. The system comprises an inflator to inflate the expandable member to an initial inflation pressure of from about 10% to about 300% of nominal pressure and a tension assembly to tension a mandrel disposed within the guidewire lumen of the expandable member, the mandrel having a proximal end portion and a distal end portion. A dispenser disposes a therapeutic agent on at least a portion of the expandable member inflated at the initial inflation pressure and a deflation station to partially deflate the expandable member to an intermediate pressure of from about 1% to about 100% of nominal pressure. A drying station to dry the therapeutic agent on the expandable member.

The methods and systems therefore can be used for manufacture and assembly of a variety of medical devices, including a drug coated balloon catheter. As noted, the expandable member has a proximal end and a distal end with a guidewire extending therebetween. In some embodiments, the expandable member can be configured with a plurality of folds defined therein. Accordingly, a reduced profile, i.e., collapsed configuration of such expandable members coincides with the folded condition. As disclosed further, the expandable member can be folded at suitable conditions to maintain the plurality of folds defined therein. The disclosed subject matter is particularly suited for coating and retaining a therapeutic agent on a folded expandable member of a medical device, without damage to the coating, during folding of the expandable member and assembly of the medical device.

Figure 1:
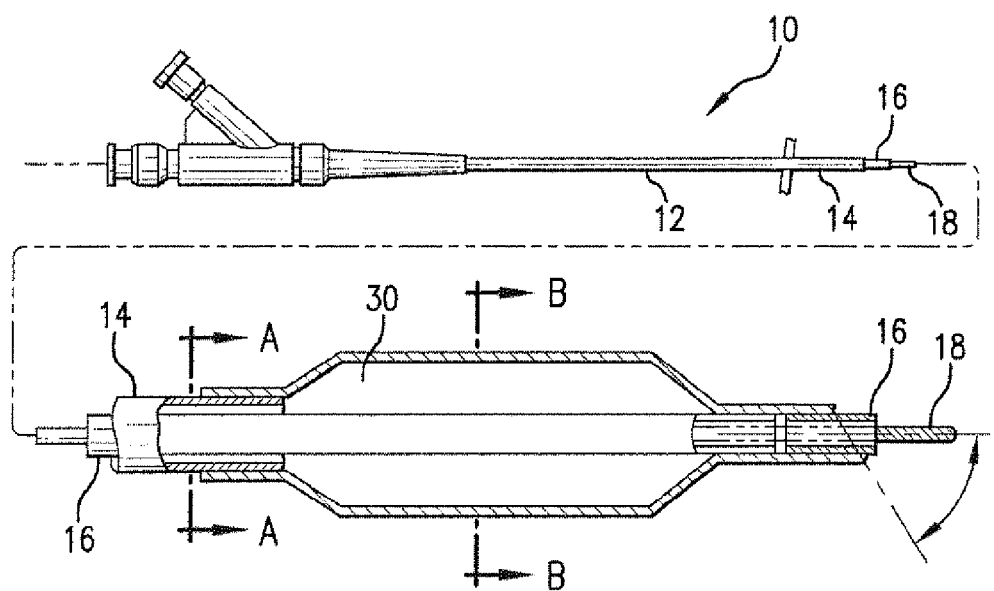
FIG. 1 is a schematic representation of an expandable member catheter in accordance with the disclosed subject matter.
Figure 1A:
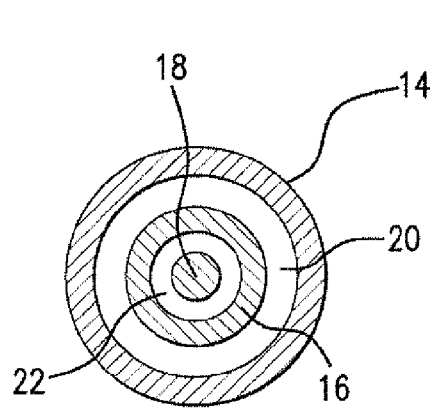
FIG. 1A is a schematic cross-sectional view taken along lines A-A in FIG. 1.
Figure 1B:
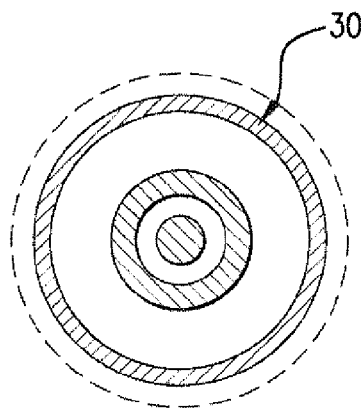
FIG. 1B is a schematic cross-sectional view taken along lines B-B in FIG. 1.
Figure 2:
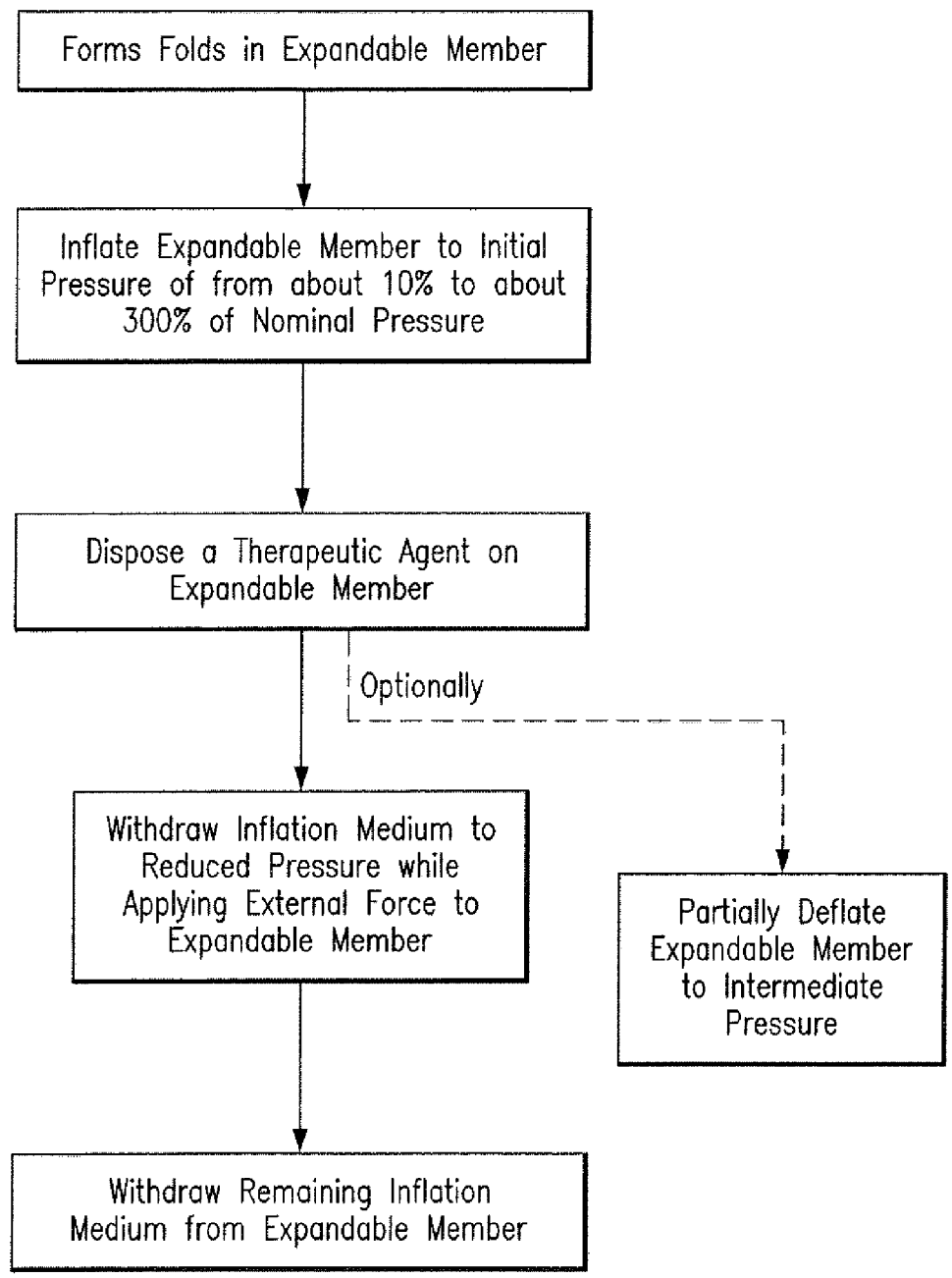
FIG. 2 is a flow chart of the method in accordance with the disclosed subject matter.

For purposes of explanation and illustration and not by way of limitation, an exemplary embodiment of a medical device having an expandable member is shown schematically in FIG. 1 including FIGS. 1A-1B. As illustrated, the medical device embodied herein is a balloon catheter 10, which includes an elongated catheter shaft 12 having a proximal end and having a distal end and an expandable member 30 located proximate the distal end of the catheter shaft. The expandable member, or balloon as depicted herein, has an outer surface and an inner surface disposed at the distal end portion of the catheter shaft.

For purpose of illustration only, a conventional coaxial over-the-wire shaft configuration is depicted. The elongated catheter shaft 12 embodied herein comprises an outer tubular member 14 and an inner tubular member 16. The outer tubular member 14 defines an inflation lumen 20 disposed between the proximal end portion and the distal end portion of the catheter shaft 12. Hence, as illustrated in FIG. 1A, the coaxial relationship of this representative embodiment defines an annular inflation lumen 20 between the inner tubular member 16 and the outer tubular member 14. The expandable member 30 is in fluid communication with the inflation lumen 20. The inflation lumen can supply an inflation medium under positive pressure and can withdraw the inflation medium, i.e., provide negative pressure, from the expandable member. The expandable member 30 can thus be inflated and deflated. The elongated catheter is sized and configured for delivery through a tortuous anatomy, and can further include a guidewire lumen 22 that permits it to be delivered over a guidewire 18. As illustrated in FIG. 1A, the inner tubular member 16 also defines the guidewire lumen 22 for the guidewire 18. Although FIGS. 1 and 1B illustrate the guidewire lumen as having a coaxial over-the-wire (OTW) construction, the catheter shaft likewise can be provided with a dual lumen shaft construction and/or a rapid-exchange (RX) construction, as is well known.

A wide variety of balloon catheters and balloon constructs are known and suitable for use in accordance with the disclosed subject matter. For example, the expandable member can be made from polymeric material such as compliant, non-compliant or semi-compliant polymeric material or polymeric blends. Examples of such suitable materials include, but are not limited to, nylon 12, nylon 11, nylon 9, nylon 6, nylon 6/12, nylon 6/11, nylon 6/9, and nylon 6/6, polyurethane, silicone-polyurethane. Examples of other balloon and catheter embodiments that can be employed in accordance with the disclosed subject matter include U.S. Pat. No. 4,748,982 to Horzewski, et al., U.S. Pat. No. 5,496,346 to Horzewski, et al. U.S. Pat. No. 5,626,600 to Horzewski, et al., U.S. Pat. No. 5,300,085 to Yock, and U.S. Pat. No. 6,406,457 to Wang et al., and U.S. patent application Ser. Nos. 12/371,426; 11/539,944; 12/371,422, each of which is hereby incorporated by reference in its entirety. Similarly, the methods and systems disclosed herein are applicable to other expandable member as known or used for medical devices.

In accordance with one aspect of the disclosed subject matter, the expandable member of the medical device can have a plurality of folds defined therein, however methods and systems of the disclosed subject matter can be used with expandable members without folds. For example, a number of conventional balloon catheters include such folds, so as to have a folded configuration and a fully expanded configuration. Generally, the formation of folds can be performed using heat and pressure to form or define creases in the material of the balloon. Examples of such folded balloons are disclosed, for purpose of illustration in U.S. Pat. No. 6,494,906 to Owens; U.S. Pat. No. 6,478,807 to Foreman, et al., and U.S. Pat. No. 5,911,452 to Yan, each of which is hereby incorporated by reference in its entirety.

Generally, a plurality of folds or pleats can be initially imparted into a expandable member of a catheter by any suitable technique known in the art. For example, this can be accomplished by processing the expandable member in a pleat head to impart a plurality of folds or pleats into the expandable member. The pleated expandable member is then processed in a fold head, wherein the pleats are wrapped in one circumferential direction and compressed to reduce overall profile. For example, the processing can be performed by an automated table top pleat and folder manufactured by Machine Solutions Inc. (MSI), MSI Balloon Form/Fold/Set Machine WS1275-101. The MSI Pleat and Fold machine pleats the expandable member at an elevated temperature (above Tg of the polymer) for a brief dwell time (10-30 s). The expandable member is then allowed to cool to room temperature. A sheath can placed over the expandable member to hold the folds in place. For purpose of illustration, the various embodiments of folded balloons are depicted herein having four or five folds of equivalent generally equivalent size, which result in a uniform shape when in the folded, i.e., uninflated, configuration. Although the exemplary embodiment illustrated in the drawings depicts four or five folds, it is to be understood that the number and size of the folds can vary, as so desired, to expandable members of various dimensions and shapes. The folded configuration provides a reduced profile, which facilitates assembly, storage and shipping of the catheter. Additionally, the reduced profile of the folded expandable member improves the deliverability and trackability of the catheter through the vascular anatomy.

In accordance with the disclosed subject matter, the expandable member is partially or fully inflated when the therapeutic agent is disposed thereon. The extent in which the expandable member is inflated depends at least in part on the amount, or pressure, of inflation medium selected for initial inflation. For example, in one embodiment, the select amount of inflation medium is sufficient to expose the surfaces of the expandable member desired to be coated or otherwise have the agent disposed thereon. Particularly, it is beneficial to apply the agent to a fully inflated expandable member to provides a larger surface area to which the agent can be applied, thus allowing for a greater amount and efficacy of coating. Although various inflation fluids are suitable for use in accordance with the disclosed subject matter, it is advantageous to employ a gaseous medium, (e.g., air, oxygen, nitrogen, etc.) to minimize any film or residue retained on the interior walls of the expandable member that can adversely affect the refolding process and final weight of the expandable member. However, as discussed further, in certain embodiments the expandable member is not fully inflated to its nominal inflation pressure. Hence, as disclosed herein, the expandable member is inflated at an initial inflation pressure of from about 10% to about 300% of nominal pressure for a given balloon size and/or material. Although identified herein as a percentage of a nominal inflation pressure, the amount of inflation can likewise be determined by a measure of volume or the like of the fully inflated balloon for the desired effect of the disclosed method and system.

An inflator or the like can be used to inflate an expandable member to the initial inflation pressure of from about 10% to about 300% of nominal pressure. For example, and with reference to conventional balloon catheters, nominal pressure generally is from about 6 atm to about 12 atm, and more particularly is from about 6 atm to about 8 atm. However, the potential pressure applied to the expandable member can actually be in the range of about 1 atm to about 24 atm.

In one embodiment of the disclosed subject matter, the expandable member is inflated to less than the fully expanded configuration and/or to an initial inflation pressure less than the nominal pressure of the expandable member. For example, the initial inflation pressure can be from about 20% to about 100% of nominal pressure, or from about 20% to about 40% of nominal pressure. Inflation of the expandable member beyond this range during the application of a coating or agent thereon can result in undesirable crack formation and deformities in the agent once dried. Additionally, by inflating to a pressure less than nominal pressure while coating, re-folding is more easily achieved because the pleat and/or fold memory is maintained.

In accordance with the disclosed subject matter, a therapeutic agent or the like is disposed on at least a portion of the outer surface of the expandable member at the initial inflation pressure. As described further, any of a variety of therapeutic agents can be applied to the surface of the expandable member. As used herein, "therapeutic agents" is broadly defined to include a wide variety of drugs, biologics, additives, polymers and mixtures thereof. Additionally, any of a variety of application techniques or methods can be used disposed the agent thereon. For example, one or more therapeutic agents can be applied to select portions of the medical device by processes such as spraying, dipping, syringe coating, electro spinning, electrostatic coating, direct coating, and direct fluid application as disclosed in U.S. patent application Ser. No. 13/108,283, combinations thereof, or other means as known to those skilled in the art. The disclosure of U.S. patent application Ser. No. 13/108,283 is hereby incorporated by reference in its entirety. The agent can be applied over at least a portion or the entirety of the expandable member or medical device in non-uniform, or uniform concentrations and/or patterns. The coating characteristics of the agent can be affected by process variables. For example, for dip-coating process, coating quality and thickness can vary as an effect of variables such as number, rate, and depth of dips along with drying time and temperature. Accordingly, the variables of the particular coating process employed can be controlled to achieve the desired coating characteristics. By way of example, and not limitation, certain coating processes that can be used with the disclosed subject matter are described in U.S. Pat. No. 7,241,344 to Worsham et al., U.S. Pat. No. 6,669,980 to Hansen, and U.S. Pat. No. 7,524,527 to Stenzel, the disclosures of which are hereby incorporated by reference in their entireties.

To assist with the application of the therapeutic agent on the surface of the expandable member, a mandrel can be inserted within the guidewire lumen 22 in FIG. 1A. The mandrel has a length sufficient to extend at least between the proximal and distal ends of the expandable member. The mandrel can be made of a variety of materials, e.g., metal, metal alloy, and polymeric material having sufficient rigidity to maintain the catheter in a linear alignment. In this regard, the mandrel serves to inhibit or prevent bowing or warping of the catheter and expandable member. Accordingly, the expandable member is maintained in a consistent and linear alignment about the longitudinal axis of the catheter, which in turn can allow for a uniform coating of therapeutic agent along the desired length of the expandable member. Furthermore, maintaining the expandable member in a fixed profile and linear alignment can assist in minimizing waste of therapeutic agent during the application process, e.g., spraying, dipping, direct fluid coating, etc. If the therapeutic agent is to be disposed on the expandable member of an assembled catheter, the mandrel can have a length sufficient to extend the entire length of the catheter and an outer diameter sized to be positioned within the guidewire lumen.

In accordance with the disclosed subject matter, the use of a mandrel provides an separate and additional benefit for the coating and refolding of an expandable member having a folded configuration. In a conventional catheter assembly, at least the distal end of the balloon is attached to the inner member of the catheter and the proximal end of the balloon is attached either to catheter shaft, so as to create an approximate 1:1 length relationship between the inner member and the balloon. During pleating and folding, the balloon is processed with heat and force in order to create the appropriately folded balloon. This heat and force treatment on the balloon occurs near the Tg of the balloon polymer material to impart the desired pleats and folds. At this temperature, the balloon material will exhibit some shrinking such that its diameter and length can slightly decrease. Depending on the size and material properties of the inner member and the balloon, this shortening in balloon length can cause a mismatch in the 1:1 length relationship between the balloon and inner member. This mismatch generally is not an issue with conventional dilatation catheters of shorter length or uncoated balloons. The pleat head equipment forms the pleats and secures the inner member as the centering axis. Subsequently, the fold head equipment causes the pleats to wrap around the inner lumen thereby keeping the balloon and inner member relatively concentric. After this, the balloon is sheathed and this completes the pleat and fold process.

Figure 9:
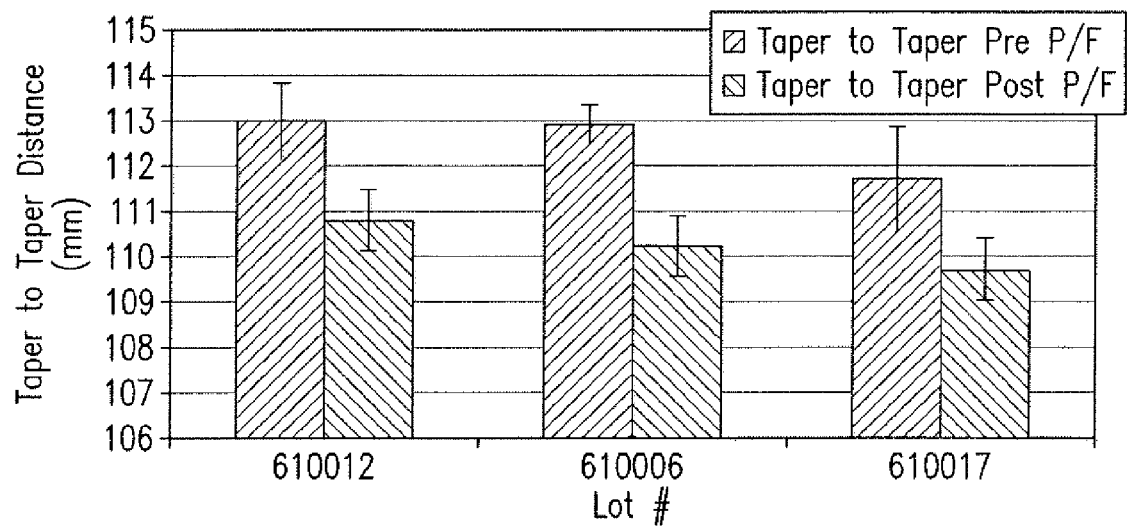
FIG. 9 is a graphical representation of an experiment showing the shortening in balloon length as a result of the pleat and fold process.
Figure 10A:
FIG. 10A is a representation of the mismatch of a short-sized balloon with a mandrel inside and FIG. 10B is a representation of the mismatch of a long-sized balloon with a mandrel inside.
Figure 10B:
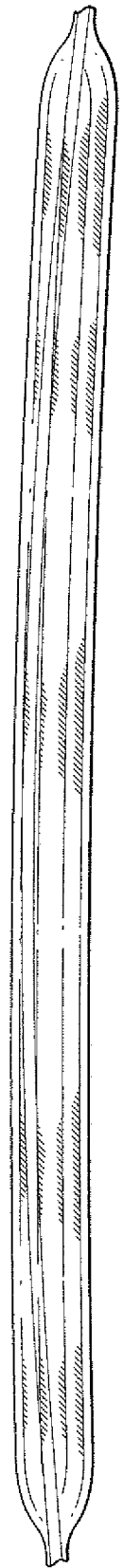

For drug coated balloons and/or balloons of greater length, such as for peripheral indications, however, manufacturing continues after the pleat and fold process, including inflating, coating, refolding and sheathing the balloon. Upon inflating a pleated and folded balloon, the mismatch between the length of the balloon and that of the inner member is observed because the inner member length remains unchanged but the shortened balloon now causes the inner member to compress resulting in a bow of the inner member away from the central axis. FIG. 9 depicts an experiment showing the shortening in balloon length of Fox sv 6×100 mm devices as a result of the pleat and fold process. For short-sized balloons (10-40 mm), the mismatch is small relative to the ratio of the length of the balloon and the inner member, and therefore often not even observed. For longer-sized expandable members (>40 mm up to 150 mm), however, the mismatch can cause a severe bow of the inner member, for example, see FIG. 10B. FIG. 10A shows the mismatch of a short-sized balloon (5×40 mm) with a mandrel inside and FIG. 10B shows the mismatch of a long-sized balloon (6×100 mm) with a mandrel inside in comparison.

Figure 11:
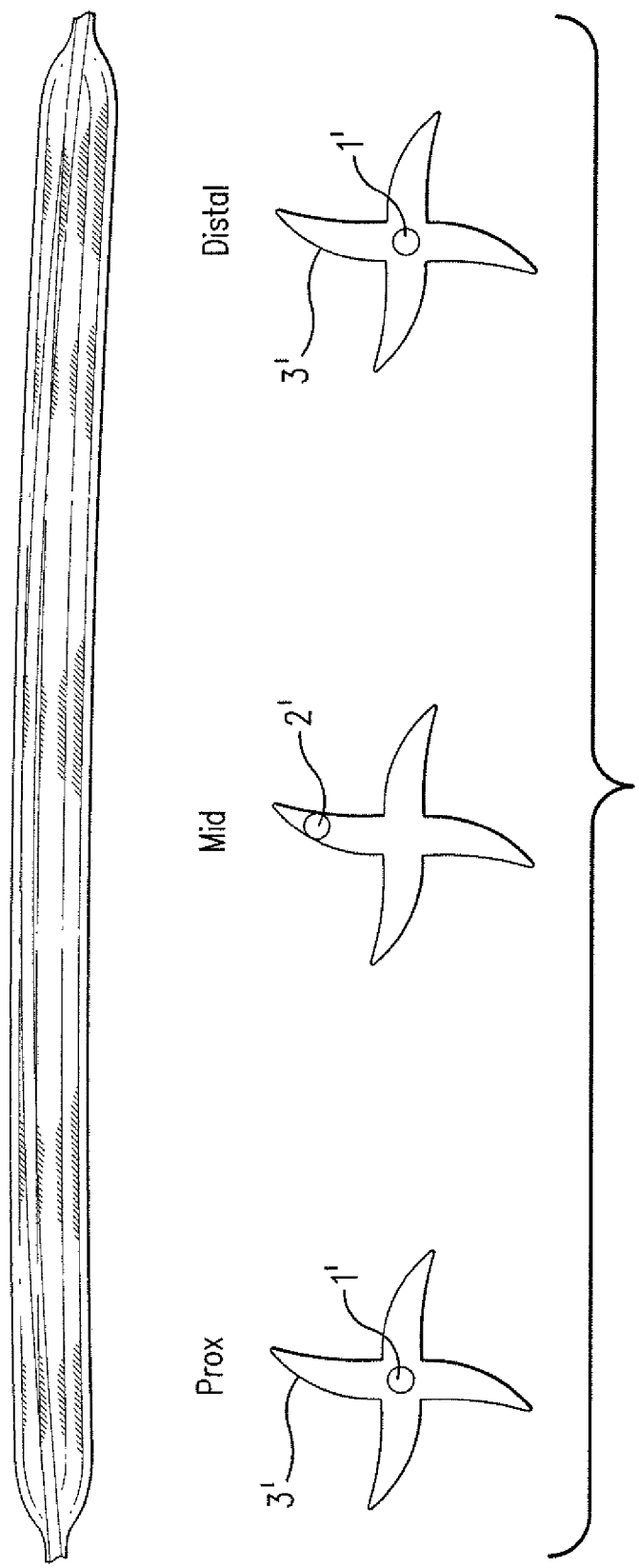
FIG. 11 is a schematic representation of biased inner member at various sections in a balloon fold.

FIG. 11 shows the issue that arises when trying to refold a balloon that has the 1:1 mismatch resulting in the bowed inner member in the balloon. Near the proximal end of the balloon, the inner member of the catheter is located at or close to the central axis 1' of the balloon because of its proximity to the proximal end joint. Along the length of the balloon, however, the inner member bows radially outward 2' into one of the folds 3' of the balloon. At the distal end of the balloon, the inner member is again aligned at or near the center axis 1' of the balloon. This bowed configuration of the inner member inhibits or prevents successful refolding of the balloon, and thus difficulty in sheathing and/or obtaining the balloon's smallest profile. During the refolding process, it is desirable to keep the inner member straight and concentric within the entire length of the balloon while reforming the initial pleats to achieve the smallest profile.

Figure 12A:
FIG. 12A is a representation of an inner member having a mandrel with applied tension and FIB. 12B is a representation of an inner member having a mandrel without applied tension.
Figure 12B:

In accordance with the disclosed subject matter, a mandrel is positioned within the guidewire lumen extending through the expandable member, and the mandrel is then tensioned to straighten the guidewire lumen (inner tubular member) within the expandable member. This aligns the guidewire lumen with the center axis of the expandable member and result in greater concentricity. FIGS. 12A and 12B show a comparison of a Fox sv 6×100 mm balloon with a pleated and folded configuration. FIG. 12A includes a mandrel under tension extending through the guidewire lumen and FIG. 12B includes a mandrel in the guidewire lumen with no applied tension. As depicted in FIG. 12A, the inner member and balloon are straighter and more concentric when tension is applied, and thus in better condition for refolding process.

Figure 13:
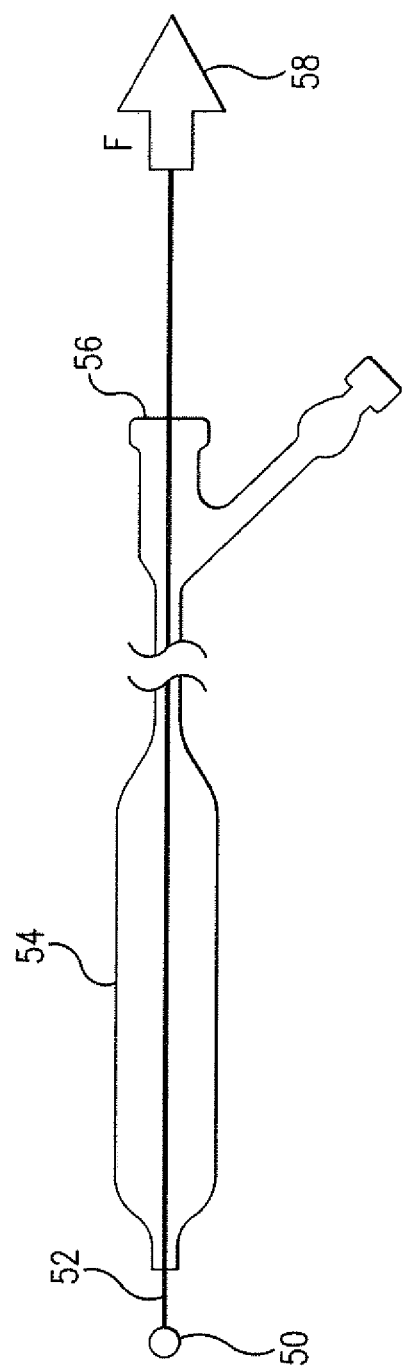
FIG. 13 is a schematic representation of system for applying tension to mandrel.

A variety of techniques can be used to apply tension to a mandrel extending through the guidewire lumen of an expandable member, such as a balloon having a folded configuration. For purpose of illustration and not limitation, a tension assembly can be provided to tension the mandrel. The mandrel has sufficient length to extend at least the length of the balloon. If working with an assembled product, such as a expandable member with a catheter shaft extending from the proximal end thereof, then the mandrel has a length sufficient to extend substantially an entire length of the guidewire lumen through the expandable member and catheter shaft. In one embodiment, as shown in FIG. 13, the tension assembly and corresponding method includes inserting a mandrel 52 into the guidewire lumen 56 with the catheter aligned axially, such as a trough or similar guide. One end portion 50 of the mandrel 52 is then fixed in position, such as be a clamp or the like, and a force 58 is applied on the other end portion of the mandrel. The force can be applied by any of variety of manual or mechanical means, including but not limited to a motor, spring, pneumatic, hydraulic or other force. This assembly tensions the mandrel within the working length of the expandable member 54, as well as the length of the guidewire lumen.

Figure 14:
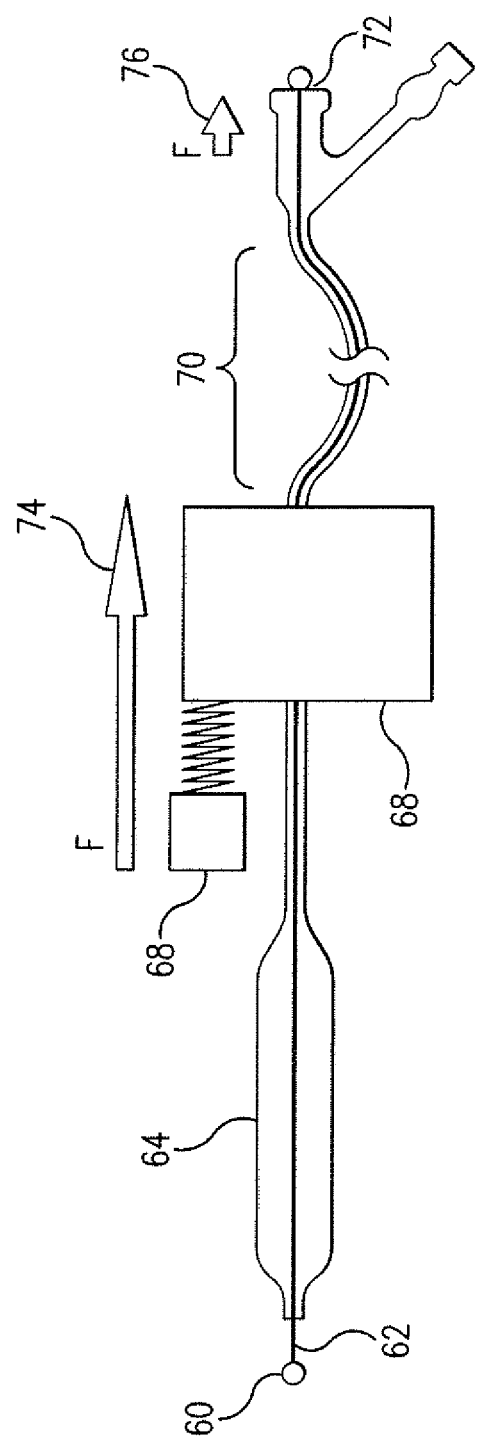
FIG. 14 is a schematic representation of an alternative system for applying tension to a mandrel.

An alternative tension assembly and corresponding method is depicted in FIG. 14. Similar to the first tensioning embodiment, a mandrel 62 is provided having a length sufficient to extend through the guidewire lumen, and one end portion 60 of the mandrel is fixed or secured in position. A stopper 72 or similar feature is provided at the other end portion of the mandrel proximate the proximal end of the catheter shaft. Tension is applied to the mandrel by urging the catheter shaft in a proximal direction into engagement against the stopper 72. The force applied by the proximal end of the catheter shaft tensions the mandrel at least within the length of the expandable member. A variety of techniques can be used to urge the catheter shaft proximally. For example, and as embodied herein, a clamp 68 or similar fastening device is secured to the catheter shaft. The clamp 68 is mounted on a linear slide and biased proximally by a spring 66, including mechanical, pneumatic and hydraulic springs. The spring 66 embodied herein generates a suitable force 74, for example approximately 2 lbs of force F, which results in a displacement of the clamp 68 along the linear slide. The catheter as a whole is urged in the proximal direction over the mandrel, such that the proximal end of the catheter shaft (e.g., the luer adaptor or sidearm assembly) applies sufficient force 76 against the stopper 72 to tension the mandrel. Since the distal end portion 60 of the mandrel 62 is fixed and the catheter is freely sliding on the mandrel, this force 76 can create slight compression on the catheter shaft 70, but tension on the mandrel. A benefit of this tension assembly and method is that suitable tension can be applied on the mandrel without requiring the catheter shaft to be aligned axially or otherwise require special arrangements when integrating with the refolding process equipment and procedure, disclosed herewith.

With the mandrel positioned in the guidewire lumen and under tension, and thus the guidewire lumen straighten, the balloon having therapeutic agent disposed thereon can be dried and refolded as desired. In accordance with an aspect of the disclosed subject matter, and in order to realize the benefits of the reduced profile for the expandable member as described above, the initial inflation pressure is at least partially released or decreased to an intermediate pressure. In this manner, the expandable member can be at least partially refolded after the desired agent is applied to or disposed on the expandable member. Likewise, the therapeutic agent can be at least partially dried on the expandable member with reduced internal stresses or cracking. To avoid detrimental impact to the applied coating or agent during the refolding process, the expandable member is first partially deflated by releasing an initial amount or pressure of inflation medium. For example, a select amount of inflation fluid or pressure, which is less than the initial inflation pressure contained within the expandable member during the coating process, is released or reduced to an intermediate pressure. Consequently, the expandable member is partially deflated.

In one embodiment, the partial deflation can be performed by exposing the expandable member to ambient conditions. That is, the expandable member in its at least partially expanded configuration and initial inflation pressure has an elevated pressure as compared to the ambient conditions. Accordingly, upon release of the initial amount of fluid, or initial inflation pressure, by exposure to the ambient conditions, the pressure differential will cause at least some of the amount of fluid contained within the expandable member to exit and reduce the pressure within the expandable member to an intermediate pressure. Thus, the expandable member will partially deflate and, if initially folded, partially refold with minimal stress imparted on the coating disposed on the surface of the expandable member. As embodied herein, the pressure release for partial deflation of the expandable member is performed within about 10 seconds or sooner.

Alternatively, an amount of fluid or pressure, which is less than that during the coating process, is withdrawn from the expandable member such as by negative pressure to partially deflate the expandable member. Additionally or alternatively, an external force is applied to the outer surface of the expandable member, simultaneously while withdrawing the initial amount of inflation medium, to facilitate the deflation and provide a circumferential constraint on the expandable member. The interaction of the deflation or withdrawal of inflation fluid and the application of the external force assists with the reformation of the previously defined folds and the symmetrical expandable member profile when in the deflated configuration. Further, and as discussed above, a mandrel can be inserted into the guidewire lumen of the catheter. The mandrel can be tensioned to inhibit or prevent bowing or warping of the catheter and expandable member, and assist in maintaining the diameter and shape of the expandable member during exposure to the external force. Accordingly, the expandable member is maintained in a consistent and linear alignment about the longitudinal axis of the catheter, which in turn allows the therapeutic agent to dry in a consistent and uniform fashion on the surface of the expandable member and thus increase the efficacy of the therapeutic agent.

The negative pressure drawn on the expandable member can be, for example, between about 0.1 atm to about 0.25 atm, to reduce the pressure within the flexible member to an intermediate pressure and thus partially deflate the expandable member. In embodiments in which a negative pressure is applied to release the initial amount of fluid, or reduce the initial inflation pressure to the intermediate pressure, the negative pressure is not sufficient to withdraw the entire amount of fluid, or initial inflation pressure, in the expandable member and thus return the expandable member to the completely folded or collapsed condition. The pressure of the expandable member can be controlled to be independently optimized such that the rate of inflation and/or depressurization can be adjusted either continuously or via a step-wise function.

For purposes of withdrawing an amount of inflation medium from an expandable member, a number of known techniques in the art can be used. For example, and as embodied herein, a deflation station withdraws an amount of inflation medium from an expandable member, e.g., partial deflation an expandable member to an intermediate pressure. A deflation station that includes a deflation device, such as a syringe pump having a gas-tight syringe, can be attached to the inflation lumen of the expandable member and withdraw a volume of fluid. The deflation device allows for automated, repeatable, and controlled amounts of fluid to be withdrawn by volume from the expandable member. This is advantageous since it reduces or eliminates the variability inherent in a human operator controlled method or apparatus. Alternative devices and techniques can be used for withdrawing desired amounts of inflation medium. Withdrawing inflation medium can include allowing the inflation medium to release from the expandable member, Withdrawing inflation medium can occur at a rate of approximately 2 ml/min or less.

In one embodiment, a deflation station is configured to withdraw an amount of inflation medium from the inflated expandable member and to apply an external force to the expandable member. With regard to the application of external force on the expandable member, a variety of known techniques in the art can be used. Particularly, the external force can be applied mechanically, hydraulically or pneumatically. For example, pneumatic force can be applied using a pressure chamber of suitable construct to induce a positive pressure on the external surface of the expandable member. Similarly, hydraulic pressure can be applied using suitable liquid that will not interact with the applied coating, or by providing a sheath to protect the applied coating. In this manner, the external force can be applied as substantially uniform pressure across the surface of the expandable member.

Figure 7:
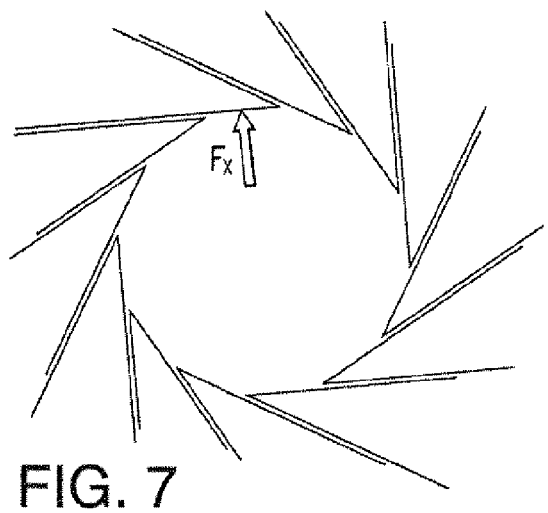
FIG. 7 is a schematic representation of an iris for imparting an external force in accordance with the disclosed subject matter.

As embodied herein, for purpose of illustration, and by no way of limitation, the external force is applied mechanically. In this manner the external force can include a torsional component to assist with the wrapping and folding of the folds. Furthermore, if desired, the mechanical force can be applied at select locations to minimize any risk of damage to the coating while obtaining the advantage of the external force. For example, a stent crimper or similar apparatus can be used for applying an external force. The stent crimper includes a plurality of jaws that allow for circumferential constraint of the expandable member. The jaws of the stent crimper can be configured to circumscribe the entire outer surface of the expandable member, or alternatively, have discrete points of contact with the expandable member. For example, a stent crimper can apply an external force to an expandable member from about 0.2 to about 0.25 PSI per mm of the expandable member. Alternatively, an external force Fx can be applied using a plurality of blades and configured with a cam or actuator to contract the blades in unison, i.e., simultaneously, such as an iris as illustrated in FIG. 7. The blades can be arranged to contact the expandable member over the entire working length of the expandable member, or alternatively, at discrete locations.

Accordingly, the jaws or blades exert a substantially uniform or non-uniform force along the expandable member, as so desired. In this manner, the stent crimper, or other suitable device, represents the sole piece of equipment that contacts the coating disposed on the expandable member. As compared to prior art techniques, this discrete point of contact is advantageous as it minimizes the risk of damage or degradation to the coating surface. In one embodiment, an external force is applied simultaneously while withdrawing the initial amount of inflation medium. Similarly, in one embodiment, an external force is performed uniformly throughout the withdrawing process, but with only sufficient force to refold the folds of the expandable member. The external force should not overcome the withdrawing process, i.e., the external force should not force inflation medium from the expandable member or otherwise crush the expandable member.

For purpose of example, and again with reference to the stent crimper, it is suitable to use a lever arm to actuate the jaws to close via gravitational forces. This is advantageous in that it results in minimal force on the expandable member, and relatively low pressure and temperature acting on the coating to thereby minimize the risk of damage or degradation of the coating. Alternatively, the jaws can be actuated hydraulically or pneumatically to induce a greater force on the expandable member, if so desired.

Further, in accordance with the disclosed subject matter, the remaining or residual amount of inflation medium, i.e., intermediate pressure, is withdrawn after drying the therapeutic coating or partially refolding the expandable member. For example, and as embodied herein, an indeflator or vacuum box is provided to draw a vacuum on the expandable member. The indeflator or vacuum box is provided in fluid communication with the inflation lumen of the expandable member, after partial deflation of the expandable member by withdrawing an initial amount of fluid medium. Additionally or alternatively, and as previously described, the remaining or residual inflation medium can be withdrawn by application of an external force to return the expandable member to the folded configuration. The external force can be in the form of a mechanical, hydraulic or pneumatic force or combination thereof as previously described. For example, a mechanical force can be applied to the expandable member in combination with the vacuum to uniformly depress the folds. Application of the mechanical force can be required depending upon the material of the expandable member and its memory. As an example, the mechanical force may be applied by a hand-crimper.

Reference will now be made to one system of the disclosed subject matter, and the operation of the system. Particularly, for purpose of illustration, and by no way of limitation, a suitable system for performing the method previously described is provided below.

In operation, a 5 cc glass tight syringe pump of the deflation device is attached to a 3-way stopcock, with the two remaining ports being attached to the vacuum source and catheter, respectively. The stopcock is open to the syringe and the proximal inflation luer of the catheter to establish a closed system. The jaws of the closure device, e.g., stent crimper, are opened to receive the inflated expandable member therein. The jaws can be configured to receive a variety of expandable member diameters, and extend a length equal to or greater than the length of the expandable member.

Figure 4A:
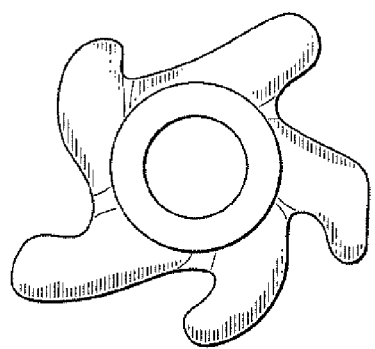
FIG. 4A is an axial view of an expandable member folded with uneven folds referred to as "pancaking"

As disclosed above, the jaws serve to circumferentially constrain the expandable member. This constraint prevents any portions of the expandable member from collapsing or refolding unevenly or "pancaking," which results in an asymmetrical profile, and uneven expansion rate of the folds upon expandable member inflation within the vessel lumen. Additionally, the circumferential constraint prevents undesired bowing or sagging of the expandable member along its longitudinal axis. An example of this uneven refolding or "pancaking" is illustrated in FIG. 4A. To further minimize or prevent "pancaking" and assist in returning the initial folds to their original direction, the external force applied by the jaws can include a torsional component that wraps or rolls the folds in an overlapping manner to minimize the profile of the expandable member. Additionally, and as described above, a mandrel is positioned within the guidewire lumen of the expandable member and tensioned to straighten the guidewire lumen within the length of the expandable member.

Upon closure of the jaws around the inflated expandable member and application of the constraining force on the outer surface of the expandable member, the deflation device gradually withdraws a predetermined amount of fluid from the expandable member at a predetermined rate to partially deflate the expandable member. In other words, the withdrawal of the amount of fluid and the application of the external force occur simultaneously. The particular amount and rate of withdrawal can vary depending on the coating properties. For example, a volume of about 0.75 ml of fluid can be withdrawn at a rate of about 2 ml/min or less for a 6×40 mm balloon. In accordance with the disclosed subject matter, the initial amount of fluid withdrawn is about 60-80% of the fluid required to inflate the expandable member to the fully expanded configuration at a rated nominal pressure.

As the deflation device is arranged to only partially deflate the expandable member, the amount of fluid withdrawn from the expandable member is less than the total amount of fluid contained within the expandable member when in inflated configuration.

Figure 4B:
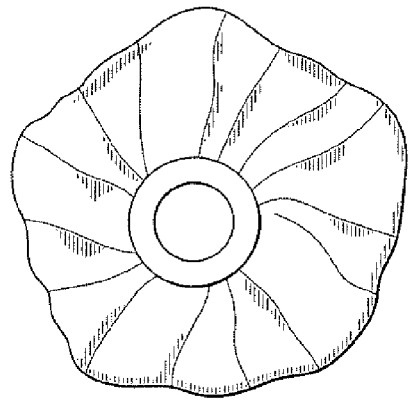
FIG. 4B is an axial view of an expandable member in an expanded configuration and FIG. 4C is an axial view of the expandable member of FIG. 4B that is refolded without application of an external force of the disclosed subject matter.
Figure 4C:
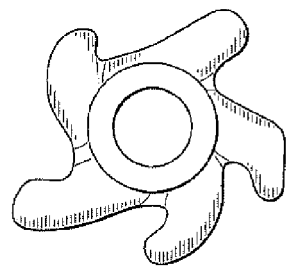
Figure 4D:
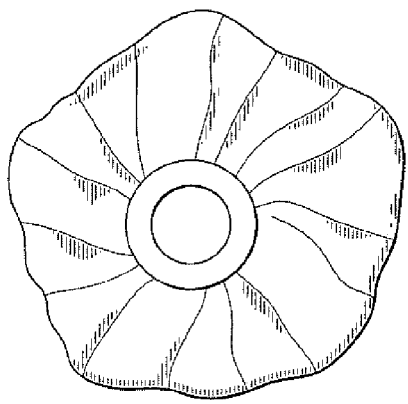
FIG. 4D is an axial view of an expandable member in an expanded configuration and FIG. 4E is an axial view of the expandable member of FIG. 4D that is refolded with application of an external force of the disclosed subject matter.
Figure 4E:
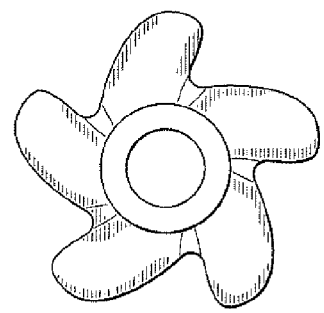

After partially deflating the expandable member by withdrawing the initial amount of fluid and closure of the jaws, the expandable member can be inspected to ensure proper refolding has occurred and no "pancaking" effects are present. FIGS. 4B and 4C provide an illustrative example of an expandable member that is refolded without the closure device, e.g., stent crimper. By comparison, FIGS. 4D and 4E provide an illustrative example of an expandable member that is refolded with the closure device, e.g., stent crimper in accordance with the disclosed subject matter. As is evident, the expandable member of FIG. 4E that is refolded in accordance with the disclosed subject matter achieves an even and symmetrical, i.e., cylindrical, shape. In the event that pancaking effects are detected during the inspection, the expandable member can be inflated again and the above-described process can be repeated to achieve an even, symmetrical refolded expandable member. In this regard, the disclosed subject matter is advantageous in that it allows for "pancaked" expandable members to be "re-worked" or reprocessed to achieve the proper symmetrical shape rather than discarded.

If no "pancaking" is detected, the vacuum source can be activated to withdraw the remaining amount of fluid within the expandable member to fully collapse the expandable member. In some embodiments, a sheath can be placed over the expandable member. In such embodiments, one end of the sheath can be flared, in order to facilitate insertion of the expandable member therein and avoid any undesired snagging, and placed over the distal end of the expandable member. Additionally, a lubricious coating can be applied to reduce the frictional forces, provided the lubrication employed does not interfere or compromise the efficacy of the therapeutic agent. The sheath is slid over the expandable member a desired distance, until significant resistance is felt. Once the sheath is in the desired position, the stopcock is opened to the vacuum source, e.g., indeflator and a full vacuum is pulled to remove all residual fluid in the expandable member. The remainder of the sheath can then be advanced over the expandable member to ensure that no wrinkles or unwanted folds are present. In another embodiment, the sheath may be applied after the vacuum compresses the expandable member.

Based upon the methods and systems disclosed herein, any of a variety of compositions or agent can be applied to the expandable member. For example, the therapeutic agent can be for treatment of tissue. Examples of suitable therapeutic agents include anti-restenosis, pro- or anti-proliferative, anti-inflammatory, antineoplastic, antiplatelet, anti-mitotic, anti-coagulant, anti-fibrin, cytostatic, cytoprotective, ACE inhibiting, cardioprotective, antithrombotic, antimitotic, antibiotic, antiallergic and antioxidant compounds. Such therapeutic agents can be, again without limitation, a synthetic inorganic or organic compound, a protein, a peptide, a polysaccharide and other sugars, a lipid, DNA and RNA nucleic acid sequences, an antisense oligonucleotide, an antibody, a receptor ligand, an enzyme, an adhesion peptide, a blood clot agent including streptokinase and tissue plasminogen activator, an antigen, a hormone, a growth factor, a ribozyme, and a retroviral vector. In some embodiments, the therapeutic agents include a cytostatic drug. The term "cytostatic" as used herein means a drug that mitigates cell proliferation but allows cell migration. The cytostatic drugs include, for the purposes of illustration and without limitation, macrolide antibiotics, rapamycin, everolimus, zotarolimus, biolimus A9, deforolimus, AP23572, myolimus, novolimus, tacrolimus, temsirolimus, pimecrolimus, structural derivatives and functional analogues of rapamycin, structural derivatives and functional analogues of everolimus, structural derivatives and functional analogues of zotarolimus, and any macrolide immunosuppressive drugs. The term "antiproliferative" as used herein means a drug used to inhibit cell growth, such as chemotherapeutic drugs. Some non-limiting examples of antiproliferative drugs include taxanes, paclitaxel, and protaxel.

Examples of anti-inflammatory drugs include both steroidal and non-steroidal anti-inflammatories (NSAID) such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopro-fen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isofluopredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Additionally or alternatively, the agent can include other compounds or additives, such as excipients, binding agents, plasticizers, solvents, surfactants, additives, fillers, and the like. Examples of possible compounds include polyvinylpyrrolidone, gelatin, maltrodextrin, starch, hydroxypropyl methyl cellulose, glycerol, polyethylene glycol, polysorbates, tweens, polyoxamers, Vitamin E TPGS, fatty alcohols, fatty esters, tocopherols, and phospholipids. In one embodiment, the therapeutic agent can be provided in liquid form or dissolved in a suitable solvent. In another embodiment, therapeutic agent is provided as a particulate and mixed in a suitable carrier for application as a fluid.

Figure 3A:
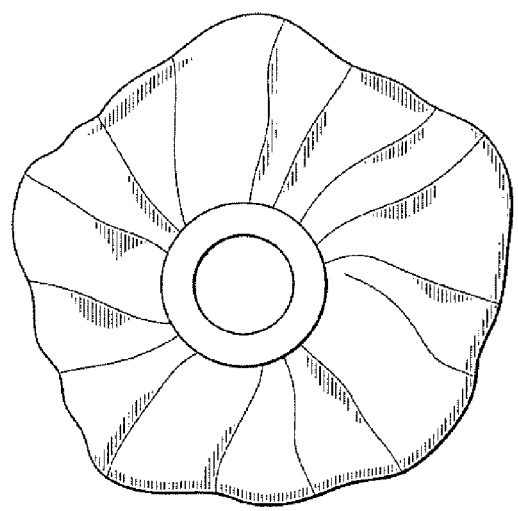
FIG. 3A is an axial view of an expandable member that is coated and dried in the expanded configuration.

As discussed above, and as illustrated in FIG. 3A, conventional techniques for coating and folding of an expandable member require the expandable member be coated in the fully expanded configuration and thereafter dried in this same fully expanded configuration. Consequently, upon refolding the expandable member, the dried and brittle coating is often damaged and/or displaced due to the compressive forces exerted on the brittle and inflexible coating during the refolding process. This damage and/or loss of coating on the expandable member thereby compromise the efficacy of the medical device.

Figure 3B:
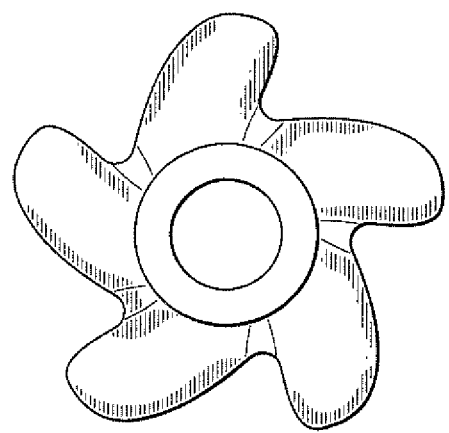
FIG. 3B is an axial view of an expandable member that is coated in an expanded configuration and partially refolded prior to drying in accordance with the disclosed subject matter.

Therefore, and in accordance with another aspect of the disclosed subject matter, the agent or coating applied to the external surface of the expandable member is allowed to dry while the expandable member is in the partially collapsed or folded configuration. In the example shown in FIG. 3B, an initial amount of inflation medium was withdrawn after the coating was applied and still in a malleable or free flowing, e.g., wet, state. The flexibility exhibited by the coating in this state allowed for greater retention of the agent or coating on the expandable member since the forces exerted on the coating during the initial or partial refolding can be absorbed or distributed within the coating layer. For purpose of example and not limitation, in one embodiment a drug dosage of about 10-600 µg/cm² and a coating thickness of about 1-40 µm was applied. The viscosities of conventional coating solutions are generally low, however, laminar flow at Reynold's numbers less than 2,300 should be maintained if a direct coating application is used for uniform coating and maintaining a continuous stream.

Upon releasing the initial amount of inflation medium to achieve the intermediate pressure, thereby partially deflating and refolding the expandable member, the expandable member can be exposed to a drying environment to evaporate a solvent contained within the coating solution. For example, the drying environment can include an oven configured to receive the entire expandable member and apply a heat to the entire surface area of the expandable member and agent applied thereto. As discussed further, a mandrel can be inserted into the guidewire lumen of the catheter. The mandrel serves to inhibit or prevent bowing or warping of the catheter and expandable member, as well as straighten the guidewire lumen within the expandable member upon application of a tensioning force. Accordingly, the expandable member is maintained in a consistent and linear alignment about the longitudinal axis of the catheter, which in turn allows the therapeutic agent to dry in a consistent and uniform fashion on the surface of the expandable member, thus maximizing the efficacy of the therapeutic agent. The mandrel can be configured with a length to extend at least the length of the expandable member, and an outer diameter for positioning within the guidewire lumen. The drying temperature and dwell time will vary depending upon the solvent formulation used, the maximum temperature being limited by drug presence on the expandable member. In one embodiment, a temperature of 50° C. and dwell time of 1 hour are for acetone/ethanol solvent evaporation. In some embodiments, the ranges for temperature and dwell time are 30°-60° C. and 5 minutes to 2 hours, respectively. Pressure is also to be considered for solvent evaporation and coating drying. For example, some slow evaporating solvents would require a vacuum of approximately 25 Inches of mercury (in Hg) and 30°-60° C. drying temperature for multiple hours. Additionally, or alternatively, a plurality of nozzles can be arranged to impart a controlled stream of air to select portions of the expandable member. This allows for non-uniform or patterned drying of the coating such that, for example, a middle portion of the expandable member can be dried at a different rate, temperature or for a different period of time, than the end portions of the expandable member, if so desired. The drying nozzles can employ air at ambient conditions, or alternatively include a heat source to provide air at elevated temperatures.

Figure 8:
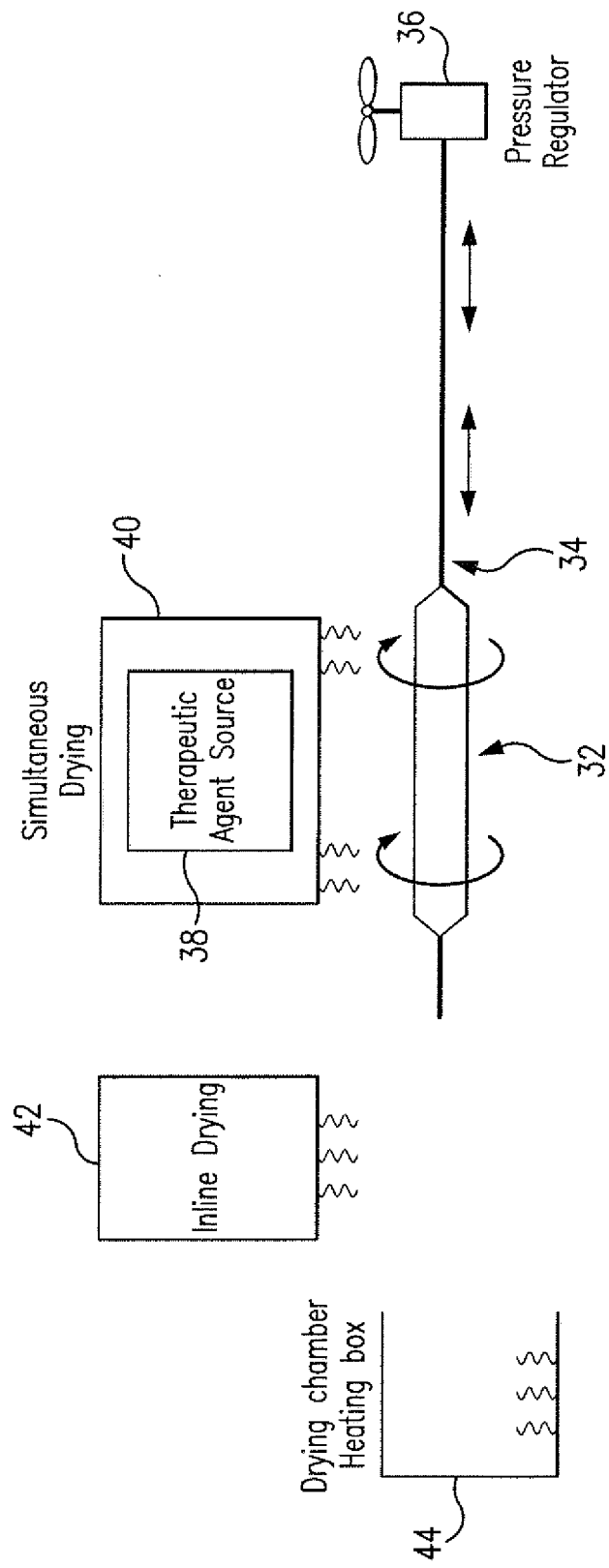
FIG. 8 is a schematic diagram of a system in accordance with the disclosed subject matter.

In further accordance with the disclosed subject matter, the drying operation can be performed in a sequential or temporal order with respect to the coating, e.g., after the agent has been disposed. Alternatively, the drying operation can be performed simultaneously and/or intermittently with the coating process. As shown in FIG. 8, an expandable member 32 is attached to a catheter 34 that is connected to a pressure regulator 36. The pressure regulator 36 monitors and regulates the pressure within the expandable member 32. A dispenser 38 disposes a therapeutic agent to at least a portion of the expandable member inflated at an initial inflation pressure during the coating process. A drying station operates to dry the therapeutic agent on the expandable member. A drying station can be provided to apply heat, forced gas, cold temperature, vacuum, infra-red energy, microwave energy, or a combination thereof to the surface of the expandable member. A simultaneous drying station 40 can be performed simultaneously with the coating process. Alternatively, or additionally, an inline drying station 42 positioned downstream of the dispenser can be performed to dry the expandable member 32. Furthermore, a drying station 44 can be performed to dry the expandable member 32 after the coating process has been completed. By way of example, and not limitation, a drying and coating processes of an expandable member that can be used herewith is described in U.S. patent application Ser. No. 13/108,283, the disclosure of which is hereby incorporated by reference in its entirety. Similarly, additional coating processes, and/or release of the inflation medium, can be performed after a drying operation, if so desired.

In accordance with another aspect of the disclosed subject matter, the coated expandable member can be exposed to an environment that facilitates plasticizing the coating. The plasticizing environment can include a relative humidity or solvent vapor atmosphere, as so desired. In one embodiment, the plasticizing environment has a temperature in the range of from about 20° C. to about 110° C., and a solvent vapor pressure in the range of from about 10 torr to about 1,520 torr. In some embodiments, the environment would expose the coated expandable member to fluid in a gaseous, vapor, or liquid state. The fluids include acetone, MEK, water, methanol, ethanol, isopropyl alcohol, diethyl ether, tetrahydrofuran, ethyl acetate. Volatile solvent has a vapor pressure at ambient temperature of at least about 0.6 torr. In one embodiment, exposure of the coated expandable member to such an environment occurs after the agent is disposed on the surface of the expandable member and prior to release of the initial amount of inflation medium to partially deflate/refold the expandable member. The duration of treatment embodied here can be between approximately 1 to 60 minutes.

The expandable member is partially deflated to an intermediate pressure during one or more of the various drying options above. In one embodiment, the expandable member is partially deflated and partially refolded with minimal surface tension exhibited on the agent or coating disposed on the surface of the expandable member. To determine whether the agent or coating retained on the expandable member meets the desired criteria, a visual inspection of the expandable member for any grossly missing drug or bare spots can be performed. A drug content analysis by high performance liquid chromatography (HPLC) also can be performed on the finished product. Additional inspection or testing can be performed using conventional analytics.

Figure 5:
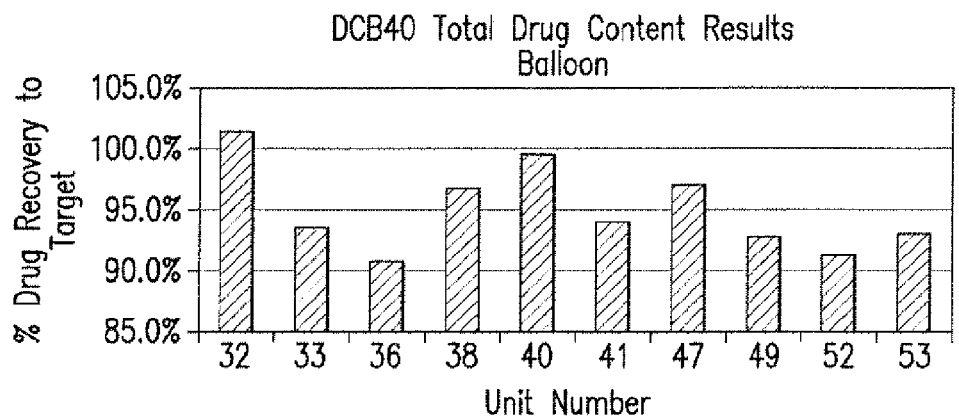
FIG. 5 is a graphical representation of the coating content of the expandable member after a sterilization process.

The methods and apparatus of the disclosed subject matter provide an additional benefit in terms of drug recovery from the folded expandable members. FIG. 5 shows data from devices that were processed using the methods disclosed. The graph depicts total drug content on the balloon after the sheath is removed and demonstrates that minimal drug is lost from the method disclosed herein. Current specifications for drug content are +/−20% from a 100% target. It is possible that particular samples have more than 100% drug as there is acceptable variability on the method for which the coating is deposited as well as acceptable variability on the analytical method used to determine drug content.

Figure 6:
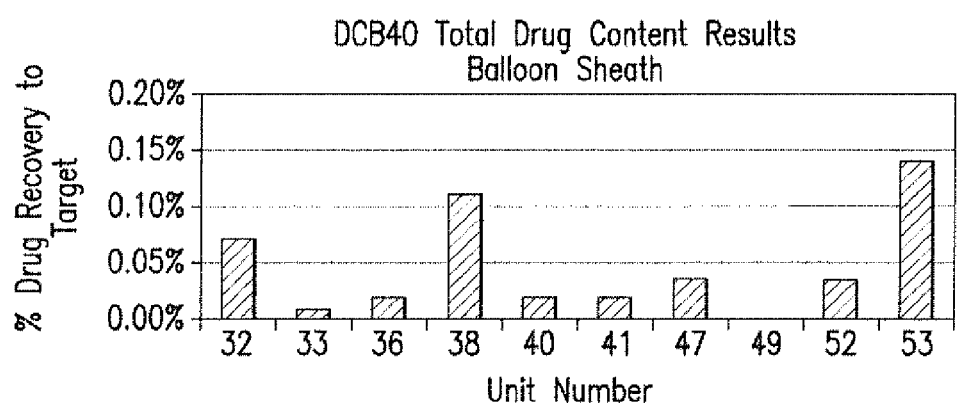
FIG. 6 is a graphical representation of the coating content of the sheath after a sterilization process.

In accordance with another aspect of the disclosed subject matter, the fully assembled catheter can undergo a sterilization process. For purpose of evaluation, a study was performed to determine the effectiveness of the presently disclosed method and system. A group of Nylon/Pebax 72D blend balloons (size 6×40 mm) were tested in this study. A 600 µg/cm$^2$ dose of zotarolimus/poly(N-vinyl pyrrolidone) (PVP)/glycerol (ZPG) formulation was applied to the balloons. After sterilization, the expandable member and sheath were removed from the catheter and were independently analyzed to determine the coating content, i.e., the amount of coating retained on the surface as a percentage of the total amount of coating dispensed during application of the coating to the expandable member. FIGS. 5 and 6 graphically depict the coating content of the expandable member and sheath, respectively, for a representative example performed using the method and system previously described. As illustrated, the method and apparatus of the disclosed subject matter provide about 90-100% drug recovery on the expandable member itself, while less than about 2% of the drug is retained on the sheath. In accordance with the disclosed subject matter, an endoprosthesis, e.g., stent, can be mounted on the expandable member. The type of stent that can be used includes, but is not limited to, bare metal stent, drug eluting stent, prohealing stent, and self-expanding vulnerable plaque implant. The stent can thus be used to provide a sustained release of drug. The stent coating can contain the same or different therapeutic agents from the catheter or expandable member. Similarly, the coating on the catheter or expandable member can have the same or distinct release kinetics from the therapeutic coating on the stent. The coating applied to the expandable member can be allowed to dry prior to placement of the stent thereon.

Alternatively, the stent can be mounted or crimped on the expandable member before the agent or coating is allowed to dry or cure past a "tacky" state. In this manner, the agent or coating can form an adhesion to help retain the stent or endoprosthesis on the expandable member. This process increases the retention of the prosthesis onto the expandable member (acting as a prosthesis retention enhancer) thus reducing the chance that the stent will move on the expandable member during the torturous delivery through the vascular lumen.

If desired, and as previously discussed, a protective sheath can be provided to protect the coating during shipping and storage and/or during delivery of the coated expandable member through the body lumen. A variety of sheaths are known, including removable sheaths or balloon covers, retractable sheaths to be withdrawn prior to deployment of the balloon, and elastic sheaths that conform to the balloon upon expansion. Such elastic sheaths are porous or include apertures along a portion thereof. In operation, the inflation of the expandable member causes the sheath to expand for release of the coating and/or therapeutic agent through the porous wall or apertures to the tissue of the arterial wall. For example, see U.S. Pat. No. 5,370,614 to Amundson, the disclosure of which is incorporated by reference in its entirety.

While the disclosed subject matter is described herein in terms of certain exemplary embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method of coating an expandable member comprising:
providing an expandable member having a proximal end and a distal end with a guidewire lumen extending therebetween, the expandable member having a deflated configuration and a fully expanded configuration at a nominal pressure;
inflating the expandable member to an initial inflation pressure of from about 10% to about 300% of nominal pressure;
positioning a mandrel within the guidewire lumen, the mandrel having a proximal end portion and a distal end portion;
tensioning the mandrel to straighten the guidewire lumen within the expandable member;
disposing a therapeutic agent on at least a portion of the expandable member at the initial inflation pressure;
partially deflating the expandable member to an intermediate pressure of from about 1% to about 100% of nominal pressure; and
drying the therapeutic agent on the expandable member.

2. The method of claim 1, wherein the initial inflation pressure is from about 20% to about 100% of nominal pressure.

3. The method of claim 1, wherein the initial inflation pressure is from about 20% to about 40% of nominal pressure.

4. The method of claim 1, wherein the mandrel has a length sufficient to extend at least between the proximal end and the distal end of the expandable member.

5. The method of claim 1, wherein the expandable member further includes a catheter shaft extending from the proximal end thereof, the guidewire lumen extending through at least a portion of a length of the catheter shaft.

6. The method of claim 5, wherein the mandrel has a length sufficient to extend substantially an entire length of the guidewire lumen.

7. The method of claim 1, wherein the mandrel is made of metal, metal alloy, or polymeric material.

8. The method of claim 1, wherein tensioning the mandrel includes securing the distal end portion of the mandrel in an axial position.

9. The method of claim 8, wherein tensioning the mandrel includes applying a tension force in a proximal direction at a select location of the mandrel.

10. The method of claim 9, wherein the expandable member further includes a catheter shaft extending from the proximal end thereof, and tensioning the mandrel includes positioning a stopper at the proximal end portion of the mandrel and urging the catheter shaft in the proximal direction in engagement against the stopper.

11. The method of claim 10, wherein the tension force is applied by a spring mounted to a fastening device configured to be secured to the catheter shaft.

12. The method of claim 11, wherein the fastening device is a clamp.

13. The method of claim 1, wherein the intermediate pressure is from about 10% to about 50% of nominal pressure.

14. The method of claim 1, wherein drying includes exposing the expandable member to an air stream of variable temperature or flow rate.

15. The method of claim 1, wherein drying includes heating of the expandable member.

16. The method of claim 1, wherein disposing the therapeutic agent on at least a portion of the expandable member at the initial inflation pressure occurs after tensioning the mandrel to straighten the guidewire lumen.

17. The method of claim 1, wherein drying the therapeutic agent on the expandable member occurs after tensioning the mandrel to straighten the guidewire lumen.

18. The method of claim 1, further comprising after partially deflating the expandable member withdrawing a remaining amount of inflation medium from the expandable member.

19. The method of claim 1, wherein the expandable member includes a plurality of folds defined therein, the expandable member having a folded configuration when in the deflated configuration.

20. The method of claim 19, wherein partially deflating the expandable member to an intermediate pressure includes withdrawing an amount of inflation medium from the expandable member, and applying an external force to the expandable member.

21. The method of claim 20, wherein withdrawing inflation medium occurs at a rate of approximately 2 ml/min or less.

22. The method of claim 20, wherein the external force is applied to the expandable member mechanically, hydraulically or pneumatically.

23. The method of claim 20, wherein the external force is applied as a substantially uniform force.

24. The method of claim 20, wherein the external force is applied at select locations of the expandable member.

25. The method of claim 20, wherein the external force includes a torsional component.

26. The method of claim 20, wherein the external force is applied to the expandable member by a stent crimper from about 0.2 to about 0.25 PSI per mm of the expandable member.

27. The method of claim 20, wherein withdrawing inflation medium and applying the external force occurs simultaneously.

28. The method of claim 1, further comprising after partially deflating the expandable member covering at least a portion of the expandable member with a sheath.

29. A system for coating an expandable member, the expandable member having a proximal end and a distal end with a guidewire lumen extending therebetween, and the expandable member having a deflated configuration and a fully expanded configuration at a nominal pressure, the system comprising:
an inflator to inflate the expandable member to an initial inflation pressure of from about 10% to about 300% of nominal pressure;
a tension assembly to tension a mandrel disposed within the guidewire lumen of the expandable member, the mandrel having a proximal end portion and a distal end portion;
a dispenser to dispose a therapeutic agent on at least a portion of the expandable member inflated at the initial inflation pressure;
a deflation station to partially deflate the expandable member to an intermediate pressure of from about 1% to about 100% of nominal pressure; and
a drying station to dry the therapeutic agent on the expandable member.

* * * * *